United States Patent
Nakae et al.

(10) Patent No.: US 9,650,347 B2
(45) Date of Patent: May 16, 2017

(54) PROCESS FOR PRODUCING PYRIDAZINONE COMPOUND AND PRODUCTION INTERMEDIATES THEREOF

(71) Applicant: SUMITOMO CHEMICAL COMPANY, LIMITED, Tokyo (JP)

(72) Inventors: Yasuyuki Nakae, Takarazuka (JP); Akio Manabe, Takarazuka (JP); Takashi Miyamoto, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/767,533

(22) PCT Filed: Feb. 18, 2014

(86) PCT No.: PCT/JP2014/054251
§ 371 (c)(1),
(2) Date: Aug. 12, 2015

(87) PCT Pub. No.: WO2014/129612
PCT Pub. Date: Aug. 28, 2014

(65) Prior Publication Data
US 2015/0376138 A1 Dec. 31, 2015

(30) Foreign Application Priority Data
Feb. 21, 2013 (JP) ................. 2013-031766

(51) Int. Cl.
| | | |
|---|---|---|
| *C07C 237/14* | (2006.01) | |
| *C07D 237/14* | (2006.01) | |
| *C07C 67/475* | (2006.01) | |
| *C07C 69/675* | (2006.01) | |
| *C07D 237/08* | (2006.01) | |

(52) U.S. Cl.
CPC .......... *C07D 237/14* (2013.01); *C07C 67/475* (2013.01); *C07C 69/675* (2013.01); *C07D 237/08* (2013.01)

(58) Field of Classification Search
CPC .................................................. C07C 237/14
See application file for complete search history.

(56) References Cited

U.S. PATENT DOCUMENTS

| | | |
|---|---|---|
| 7,569,518 B2 | 8/2009 | Morishita et al. |
| 8,008,512 B2 | 8/2011 | Morishita et al. |
| 2011/0136762 A1 | 6/2011 | Sharpe |
| 2013/0137658 A1 | 5/2013 | Matsuzaki |

FOREIGN PATENT DOCUMENTS

| | | |
|---|---|---|
| CN | 102164485 A | 8/2011 |
| ES | 2324883 T3 | 8/2009 |
| JP | 2010-6722 A | 1/2010 |
| JP | 2012-503659 A | 2/2012 |
| WO | WO 2005/121104 A1 | 12/2005 |
| WO | WO 2007/044796 A2 | 4/2007 |
| WO | WO 2010/036553 A1 | 4/2010 |
| WO | WO 2012/020772 A1 | 2/2012 |
| WO | WO 2014/157021 A1 | 10/2014 |
| WO | WO 2014/188863 A1 | 11/2014 |

OTHER PUBLICATIONS

Office Action No. 9737 (including an English translation thereof) issued in the corresponding Colombian Patent Application No. 15187862 on Sep. 19, 2016.
Chinese Academy of Sciences, "Chiral Synthesis-Asymmetric Reactions and Users thereof", 2nd Edition, 2005, pp. 146-150 (22 pages total).
Chinese Office Action and Search Report, dated Sep. 21, 2016, for Chinese Application No. 201480009536.8, with an English translation.

(Continued)

*Primary Examiner* — Paul V Ward
(74) *Attorney, Agent, or Firm* — Birch, Stewart, Kolasch & Birch, LLP

(57) ABSTRACT

The present invention provides a process for producing a compound of the formula (1) wherein X represents a hydrogen atom, etc., and Y represents a hydrogen atom, etc., which comprises step 1 of reacting a compound of the formula (2) and a compound of the formula (3) in the presence of a Lewis acid wherein R represents a hydrogen atom, etc., to obtain an adduct, and step 2 of reacting the adduct obtained in the step 1 and hydrazine to obtain the compound of the formula (1).

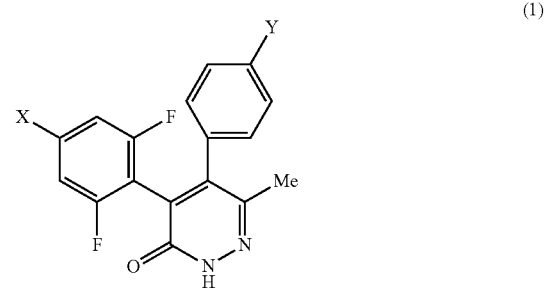

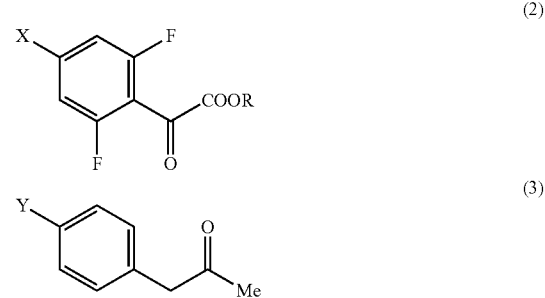

14 Claims, No Drawings

(56) References Cited

OTHER PUBLICATIONS

Extended European Search Report, issued Jun. 3, 2016, for European Application No. 14753644.5.
International Preliminary Report on Patentability and Written Opinion of the International Searching Authority issued in the corresponding International Application No. PCT/JP2014/054251 on Aug. 25, 2015.
Lamberth et al., "A new Knoevenagel-type synthesis of fully substituted •—hydroxybutenolides," Tetrahedron Letters, vol. 53, 2012, pp. 4117-4120.
Lamberth et al., "Synthesis and fungicidal activity of tubulin polymerisation promoters. Part 2: Pyridazines," Bioorganic & Medicinal Chemistry, vol. 20, 2012, pp. 2803-2810.
Mahrwald et al., "Highly Regioselective Lewis Acid-Mediated Aldol Additions at the More Encumbered •—Side of Unsymmetrical Ketones," Journal of the American Chemical Society, vol. 120, No. 2, 1998, pp. 413-414.
Office Action (including an English translation thereof) issued in the corresponding Israeli Patent Application No. 239987 on Dec. 27, 2016.

PROCESS FOR PRODUCING PYRIDAZINONE COMPOUND AND PRODUCTION INTERMEDIATES THEREOF

TECHNICAL FIELD

The present invention relates to a process for producing a pyridazinone compound and a production intermediate thereof.

BACKGROUND ART

WO 2005/121104 discloses that compounds represented by the formula (1) and the like;

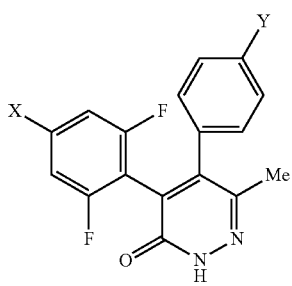

(1)

wherein X represents a hydrogen atom, a fluorine atom, a chlorine atom or a bromine atom, and Y represents a hydrogen atom, a fluorine atom, a chlorine atom or a bromine atom;
are useful as production intermediates for fungicides, and there is a desire for a useful production method thereof.

DISCLOSURE OF THE INVENTION

The present invention has an object of providing a useful process for producing a compound represented by the formula (1) and its production intermediates.

The present inventor has investigated to find a useful process for producing a compound represented by the formula (1) and resultantly found a useful process for producing a compound represented by the formula (1), leading to the present invention.

That is, the present invention is as described below.

[1] A process for producing a compound of the formula (1);

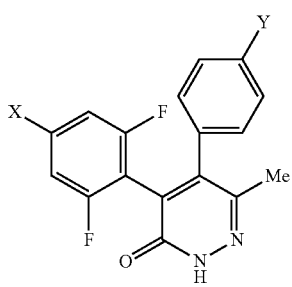

(1)

wherein X represents a hydrogen atom, a fluorine atom, a chlorine atom or a bromine atom, and Y represents a hydrogen atom, a fluorine atom, a chlorine atom or a bromine atom,
which comprises step 1 of reacting a compound of the formula (2) and a compound of the formula (3) in the presence of a Lewis acid to obtain an adduct;

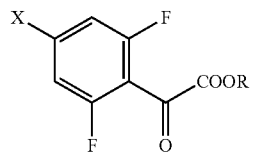

(2)

wherein R represents a hydrogen atom or a C1-C4 alkyl group and X has the same meaning as defined above,

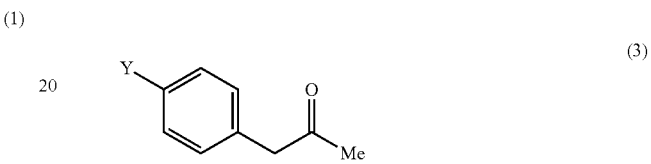

(3)

wherein Y has the same meaning as defined above;
and step 2 of reacting the adduct obtained in the step 1 and hydrazine to obtain the compound of the formula (1).

[2] The process according to [1], wherein the adduct is a compound of the formula (5);

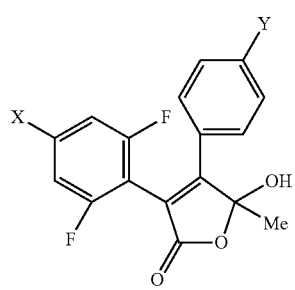

(5)

wherein X and Y have the same meanings as defined above.

[3] The process according to [1] or [2], wherein the reaction of the compound of the formula (2) and the compound of the formula (3) is conducted in the presence of an polar aprotic solvent.

[4] The process according to any one of [1] to [3], wherein Lewis acid is a titanium compound or a boron compound.

[5] The process according to any one of [1] to [4], wherein the reactions both in step 1 and step 2 are carried out in the presence of an aromatic hydrocarbon solvent.

[6] A process for producing a compound represented by the formula (1), which comprises reacting a compound of the formula (4) and hydrazine;

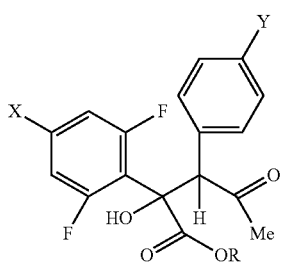

(4)

wherein X, Y and R have the same meanings as defined above.

[7] The process according to [6], wherein the reaction is carried out in the presence of an aromatic hydrocarbon solvent.

[8] A process for producing a compound of the formula (6);

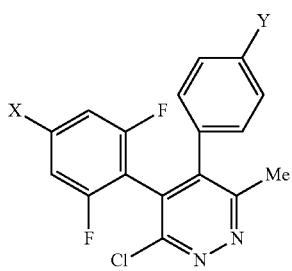

(6)

wherein X and Y have the same meanings as defined above;

which comprises step 1 of reacting a compound of the formula (2) and a compound of the formula (3) in the presence of a Lewis acid to obtain an adduct, step 2 of reacting the adduct obtained in the step 1 and hydrazine to obtain a compound of the formula (1), and step 3 of reacting the compound of the formula (1) obtained in step 2 and a chlorinating agent.

[9] A process for producing a compound of the formula (6), which comprises reacting a compound of the formula (4) and hydrazine to obtain a compound of the formula (1), and reacting the compound of the formula (1) and a chlorinating agent.

[10] A process for producing a compound of the formula (6), which comprises reacting a compound of the formula (5) and hydrazine to obtain a compound of the formula (1), and reacting the compound of the formula (1) and a chlorinating agent.

[11] A process for producing a compound of the formula (4), which comprises reacting a compound of the formula (2) and a compound of the formula (3) in the presence of a Lewis acid in range of from 20 to 80° C.

[12] The process according to [11], wherein the Lewis acid is titanium compound or a boron compound.

[13] The process according to [11] or [12], wherein the reaction is carried out in the presence of an aromatic hydrocarbon solvent.

[14] A compound of the formula (4).

According to the present invention, a compound of the formula (1) can be produced efficiently and inexpensively on an industrial scale.

MODES FOR CARRYING OUT THE INVENTION

The present invention will be explained in detail below.

"C1-C4 alkyl group" denotes a linear or branched alkyl group having 1 to 4 carbon atoms, and examples thereof include a methyl group, an ethyl group, a propyl group, an isopropyl group, a butyl group and a tert-butyl group.

Examples of "Lewis acid" includes titanium compound such as titanium tetrachloride ($TiCl_4$), tetraethyl orthotitanate {$Ti(OEt)_4$)} and tetraisobutyl orthotitanate {Ti(O-iPr)$_4$)}; aluminum compound such as aluminum chloride ($AlCl_3$), aluminum triethoxide {$Al(OEt)_3$} and aluminum triisopropoxide {$Al(O-iPr)_3$}; boron compound such as boron trifluoride, ($BF_3$) boron trichloride ($BCl_3$), boron tribromide ($BBr_3$), trimethyl borate {$B(OMe)_3$} and boron trifluoride diethyl etherate ($BF_3/(OC_2H_5)_2$); and zirconium compound such as zirconium tetrachloride ($ZrCl_4$), zirconium tetrapropoxide {$Zr(OPr)_4$} and zirconium tetrabutoxide {$Zr(OBu)_4$}. In particular, titanium compound and boron compound are preferred, and titanium tetrachloride is especially preferred.

Embodiments of the compound of the formula (4) include the following compounds.

Compounds of the formula (4) in which R is a hydrogen atom;

Compounds of the formula (4) in which X is a hydrogen atom;

Compounds of the formula (4) in which Y is a hydrogen atom or a chlorine atom;

Compounds of the formula (4) in which X is a hydrogen atom and Y is a hydrogen atom or a chlorine atom;

Compounds of the formula (4) in which R is a hydrogen atom and X is a hydrogen atom;

Compounds of the formula (4) in which R is a hydrogen atom and Y is a hydrogen atom or a chlorine atom;

Compounds of the formula (4) in which R is a hydrogen atom, X is a hydrogen atom and Y is a hydrogen atom or a chlorine atom.

The compound of the formula (1) (hereinafter, may also be referred to as compound (1)) can be produced by the following steps.

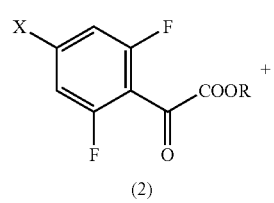

(2)

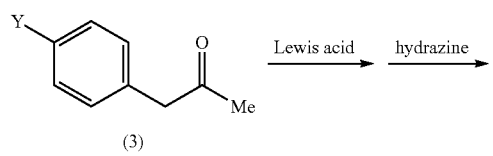

(3)

-continued

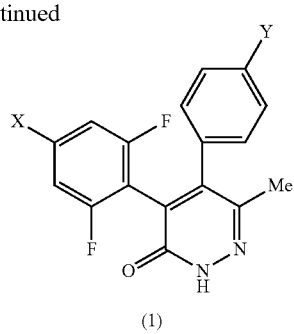

wherein X, Y and R have the same meanings as defined above.

The present invention includes a step of reacting the compound of the formula (2) (hereinafter, referred to also as compound (2)) and the compound of the formula (3) (hereinafter, referred to also as compound (3)) in the presence of a Lewis acid to obtain an adduct, and a step of reacting the adduct obtained in the above-described step (hereinafter, referred to also as adduct) and hydrazine to obtain the compound (1).

First, the step of reacting compound (2) and compound (3) in the presence of a Lewis acid will be illustrated.

The reaction is usually carried out in the presence of a solvent.

Examples of the solvent used in the reaction include hydrocarbon solvent such as toluene and xylene, halogenated aromatic hydrocarbon solvent such as chlorobenzene and 1,2-dichlorobenzene, and mixtures thereof.

Examples of Lewis acid used in the reaction include the same Lewis acids as mentioned above. The titanium compound and the boron compound are preferred, and titanium tetrachloride is more preferred. The use amount of Lewis acid is usually from 0.01 to 10 moles with respect to 1 mole of the compound (2), and preferably from 0.1 to 10 moles.

The temperature of the reaction is usually in the range of from 20 to 150° C., and the reaction time is, through varying depending on the reaction temperature, usually in the range of from 1 to 200 hours.

After completion of the reaction, the adduct can be isolated by, for example, agitating the reaction mixture with water or ice water, then, conducting extraction with an organic solvent from the agitated reaction mixture, and subjecting the resultant organic layer to an operation such as drying and concentration. The adduct can also be further purified by chromatography, re-crystallization and the like.

Though the adduct can be subjected to the reaction with hydrazine to obtain the compound of the formula (1) after isolation, it is preferred in the industrial production that the adduct be provided for the next step without purification after extraction.

Next, the reaction of the adduct and hydrazine will be described.

The reaction is usually conducted in the presence of a solvent.

Examples of the solvent used in the reaction includes alcohol solvent such as n-butanol, n-propanol, isopropyl alcohol, ethanol and methanol, aromatic hydrocarbon solvent such as toluene and xylene, halogenated aromatic hydrocarbon solvent such as chlorobenzene and 1,2-dichlorobenzene, water and mixtures thereof. Aromatic hydrocarbon solvent such as toluene and xylene are preferred.

As hydrazine used in the reaction, hydrate thereof is usually used, and the amount thereof is usually from 1 to 5 moles with respect to 1 mole of the adduct.

The reaction temperature of the reaction is usually in the range of from 0 to 120° C., and the reaction time is usually in the range of from 1 to 100 hours.

After completion of the reaction, the compound (1) can be isolated, for example, by performing such an operation as cooling down to room temperature, and then, collecting the generated solid, which is the isolated compound (1), by filtration. The isolated compound (1) can further be purified by chromatography, re-crystallization and the like.

Next, each step will be explained in detail.

The step of reacting a compound (2) and a compound (3) in the presence of a Lewis acid, to produce a compound of the formula (5) (hereinafter also referred to as compound (5)) will be further explained.

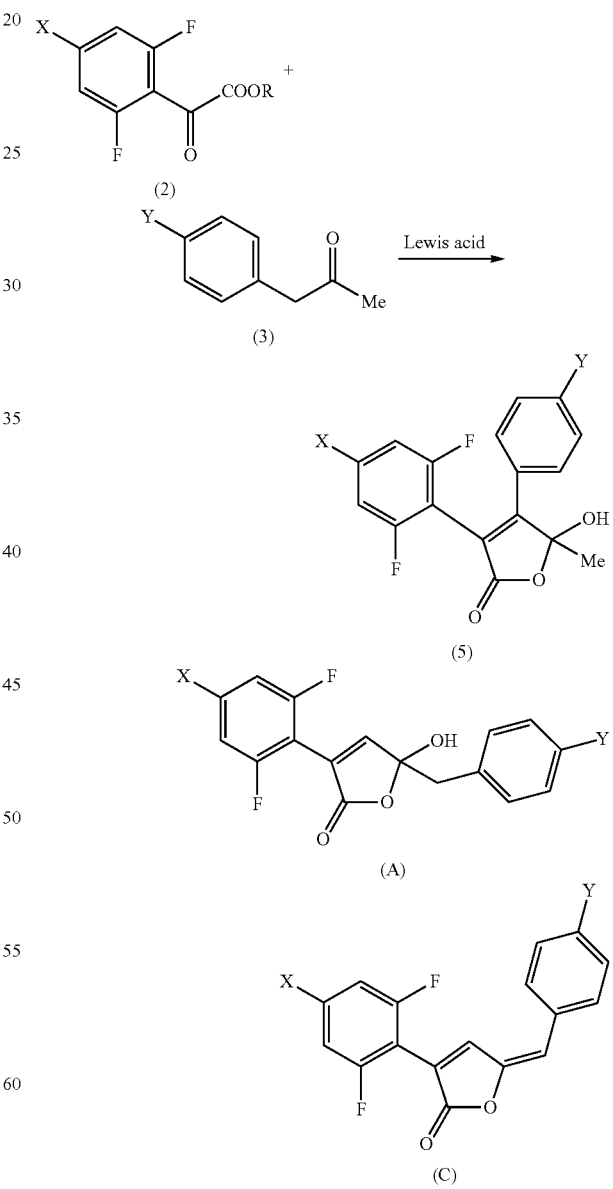

In the above formulas, X, Y and R have the same meaning as defined above.

The reaction is usually conducted in the presence of a solvent.

Examples of the solvent used in the reaction include aromatic hydrocarbon solvent such as toluene and xylene, halogenated aromatic hydrocarbon solvent such as chlorobenzene and 1,2-dichlorobenzene, hydrocarbon solvent such as hexane, heptane and octane, halogenated hydrocarbon solvent such as 1,2-dichloroethane and chloroform, ether solvent such as tetrahydrofuran, 1,2-dimethoxyethane and diisopropyl ether, and mixtures thereof. Aromatic hydrocarbon solvent such as toluene and xylene are preferred.

Examples of Lewis acid used in the reaction include the same Lewis acids as mentioned above. The titanium compound and the boron compound are preferred, and titanium tetrachloride is especially preferred. The use amount Lewis acid is usually from 0.01 to 10 moles with respect to 1 mole of the compound (2), preferably from 0.01 to 1 mole, more preferably from 0.1 to 1 mole, further more preferably from 0.1 to 0.3 moles.

In the reaction, it is preferred to add a polar aprotic solvent.

Examples of the polar aprotic solvent used include 1,3-dimethyl-2-imidazolidinone (hereinafter, referred to as DMI), 1-methyl-2-pyrrolidinone (hereinafter referred to as NMP), N,N-dimethylformamide, N,N-dimethylacetamide, triethylamine and diisopropylethylamine. DMI and NMP are preferred. The amount used of the polar aprotic solvent is usually from 0.01 to 10 moles with respect to 1 mole of the compound (2).

The temperature of the reaction is usually in the range of from 20 to 150° C., and preferably from 80 to 150° C. and the reaction time is, through varying depending on the reaction temperature, usually in the range of from 1 to 100 hours, preferably from 1 to 50 hours.

It is preferred for shortening of reaction time that water be removed from the reaction system by a dehydrating agent such as molecular sieve or by azeotropic distillation using Dean-Stark apparatus or the like. The removal of water can be conducted under reduced pressure.

After completion of the reaction, the compound (5) can be isolated by, for example, agitating the reaction mixture with water or ice water, then, conducting extraction with an organic solvent from the agitated reaction mixture, and subjecting the resultant organic layer to an operation such as drying and concentration. It is preferred that the extraction be carried out by using the same solvent as the reaction solvent. The isolated compound (5) can also be further purified by chromatography, re-crystallization and the like.

In the reaction, the compound of the formula (A) and the compound of the formula (C) are also formed.

Examples of the compound (5) include the following compounds.

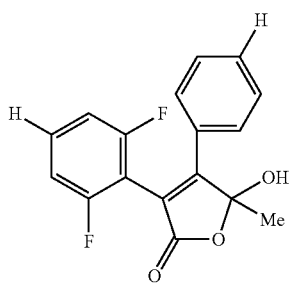

(5-1)

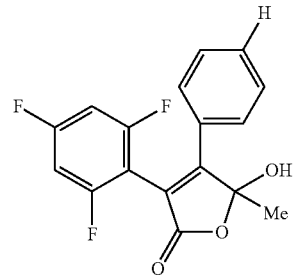

(5-2)

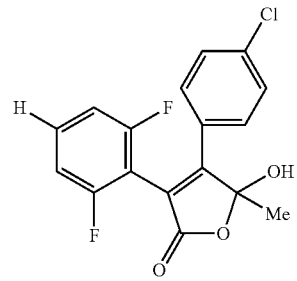

(5-3)

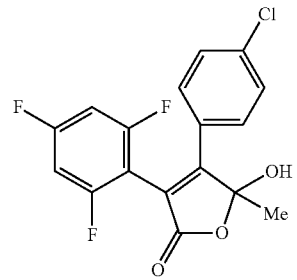

(5-4)

During the reaction, the following compounds are formed as positional isomers of the reaction product and dehydrated compounds of the positional isomers.

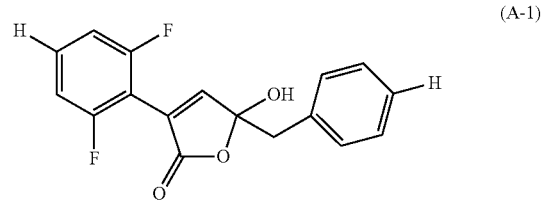

(A-1)

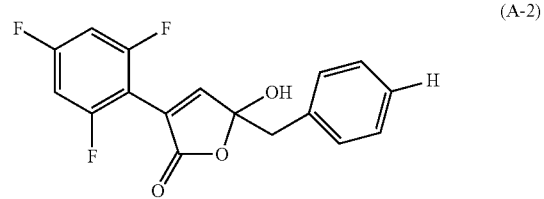

(A-2)

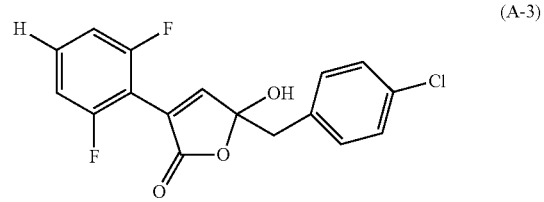

(A-3)

(A-4)
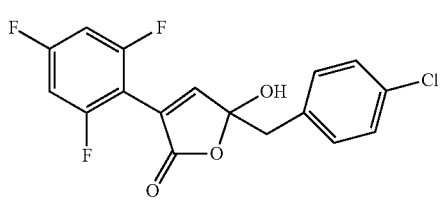

(C-1)
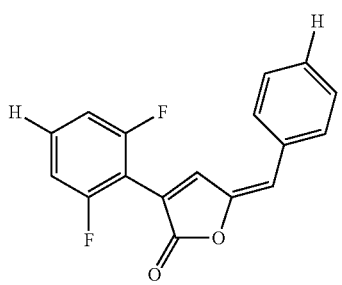

(C-2)
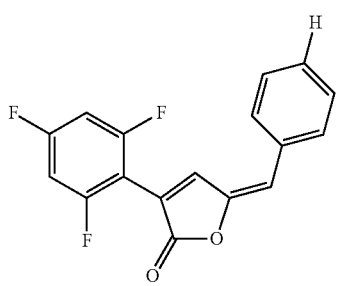

(C-3)
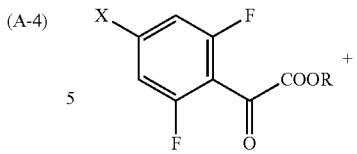

(C-4)

The step of reacting the compound (2) and the compound (3) in the presence of a Lewis acid to produce the compound (4) will be further explained.

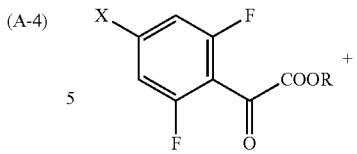
(2)

(3)

Lewis acid →

(4)

(B)

In the formulas above, X, Y and R have the same meaning as defined above.

The reaction is usually conducted in the presence of a solvent.

Examples of the solvent used in the reaction includes aromatic hydrocarbon solvent such as toluene and xylene, halogenated aromatic hydrocarbon solvent such as chlorobenzene and 1,2-dichlorobenzene, hydrocarbon solvent such as hexane, heptane and octane, ether solvent such as tetrahydrofuran, diethyl ether, 1,2-dimethoxyethane and diisopropyl ether, and mixtures thereof.

Examples of Lewis acid used in the reaction include the same Lewis acids as mentioned above. The titanium compound and the boron compound are preferred, and titanium tetrachloride is especially preferred. The use amount thereof is usually from 0.1 to 10 moles with respect to 1 mole of the compound (2), preferably from 0.5 to 10 moles, more preferably from 0.9 to 2 moles.

The reaction temperature of the reaction is usually in the range of from 20 to 80° C., and preferably from 50 to 80° C. The reaction time is, through varying depending on the reaction temperature, usually in the range of from 1 to 200 hours, preferably 1 to 100 hours.

As the amount of a compound of the formula (B) formed in the reaction as a positional isomer of the compound (4) is very low, the reaction is preferred in the production on an industrial scale.

After completion of the reaction, the compound (4) can be isolated by, for example, mixing the reaction mixture with water or ice water, then, conducting extraction with an organic solvent from the mixed reaction mixture, and subjecting the resultant organic layer to an operation such as drying and concentration. It is preferred that the extraction be carried out by using the same solvent as the reaction solvent. The isolated compound (4) can also be further purified by chromatography, re-crystallization and the like.

Though the compound (4) can be subjected to the reaction with hydrazine to obtain the compound (1) after isolation, it is preferred in the production on an industrial scale that the organic layer containing the compound (4) after extraction be provided for the next step without purification.

The compound (2) in which R is hydrogen atom can be produced, for example, from a compound of the formula (7):

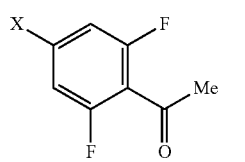
(7)

wherein X has the same meaning as defined above, according to a method described in EP 0386940 A1.

The compound (2) in which R is a C1-C4 alkyl group can be produced, for example, by reacting a compound represented by the formula (2) in which R is hydrogen atom and an alcohol of the formula (8):

R—OH (8)

wherein R has the same meaning as defined above, in the presence of an acid catalyst.

Example of the acid catalyst includes concentrated sulfuric acid, and the use amount thereof is usually of from 0.01 to 0.3 moles with respect to the alcohol of the formula (8).

The reaction temperature is usually from 20° C. to the boiling point of the compound of the formula (8).

Examples of the compound of the formula (2) include the following compounds.

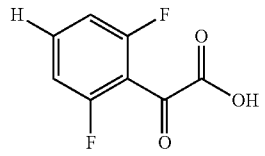
(2-a-1)

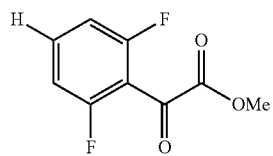
(2-b-1)

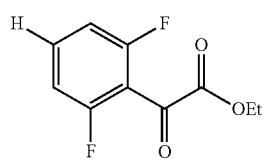
(2-c-1)

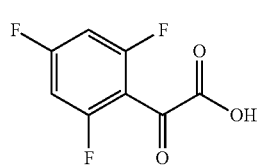
(2-a-2)

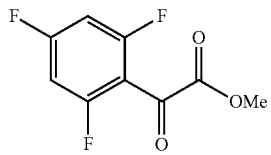
(2-b-2)

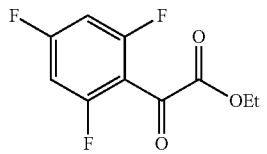
(2-c-2)

The compound (3) is publicly known. Examples of the compound (3) include the following compounds.

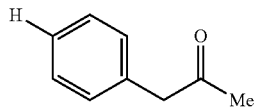
(3-1)

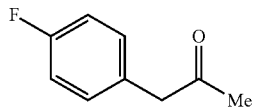
(3-2)

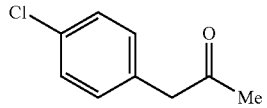
(3-3)

Next, the step of reacting the compound (4) and hydrazine to produce the compound (1) will be further explained.

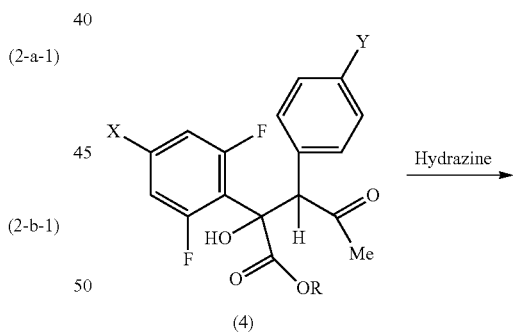

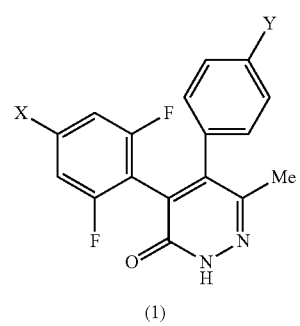

(1)

In the formulae above, X, Y and R have the same meanings as defined above.

The reaction is usually conducted in the presence of a solvent.

Examples of the solvent used in the reaction include alcohol solvent such as n-butanol, n-propanol, isopropyl alcohol, ethanol and methanol, aromatic hydrocarbon solvent such as toluene and xylene, halogenated aromatic hydrocarbon solvent such as chlorobenzene and 1,2-dichlorobenzene, hydrocarbon solvent such as hexane, heptane and octane, halogenated hydrocarbon solvent such as 1,2-dichloroethane and chloroform, ether solvent such as tetrahydrofuran, 1,2-dimethoxyethane and diisopropyl ether, water, and mixtures thereof, and aromatic hydrocarbon solvent are preferred. As the compound (4) can be provided for the reaction without condensation operation, it is preferred to use the same solvent as the solvent used in the previous step.

As hydrazine used in the reaction, a hydrate thereof is usually used, and the amount thereof is usually from 1 to 5 moles, and preferably from 1 to 2 moles with respect to 1 mole of the compound (4).

It is preferred that the reaction be conducted in the presence of an acid from the standpoint of the reaction rate.

As the acid used in the reaction, a weak acid such as acetic acid and propionic acid is usually used, and the amount thereof is usually from 0.01 to 100 moles with respect to 1 mole of the compound (4).

The reaction temperature of the reaction is usually in the range of from 0 to 120° C., and the reaction time is usually in the range of from 1 to 100 hours.

After completion of the reaction, the compound (1) can be isolated by performing an operation such as cooling down to room temperature, and then, collecting the generated solid by filtration. The isolated compound (1) can also be further purified by chromatography, re-crystallization and the like.

As the method of reacting a compound (5) and hydrazine, to produce a compound (1), example of the method includes the following method, though publicly known methods may be used.

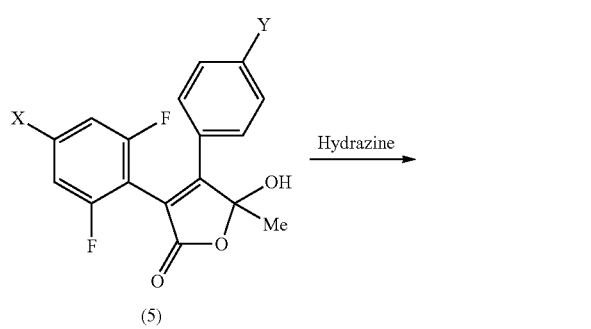

(5)

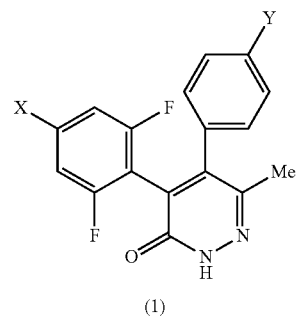

(1)

In the above formulas, X and Y have the same meanings as defined above.

The reaction is usually conducted in a solvent.

Examples of the solvent used in the reaction include hydrocarbon solvent such as hexane, heptane and octane, aromatic hydrocarbon solvent such as toluene and xylene, halogenated hydrocarbon solvent such as 1,2-dichloroethane and chloroform, halogenated aromatic hydrocarbon solvent such as chlorobenzene and 1,2-dichlorobenzene, alcohol solvent such as methanol, ethanol, propanol, isopropyl alcohol and butanol, ether solvent such as tetrahydrofuran and 1,2-dimethoxyethane, and mixtures thereof.

As hydrazine used in the reaction, a hydrate thereof is usually used, and the amount thereof is usually from 1 to 5 moles with respect to 1 mole of the compound (5).

The reaction temperature of the reaction is usually in the range of from 0 to 120° C., and the reaction time is, through varying depending on the reaction temperature, usually in the range of from 1 to 100 hours, and preferably from 1 to 24 hours.

After completion of the reaction, the compound (1) can be isolated, for example, by settling and, if necessary, cooling the reaction mixture to cause deposition of solid, and filtrating the solid, by concentrating the reaction mixture, and the like. The isolated compound (1) can also be further purified by chromatography, re-crystallization and the like.

Examples of the compound (1) include the following compounds.

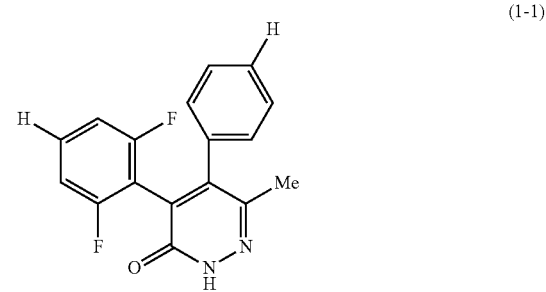

(1-1)

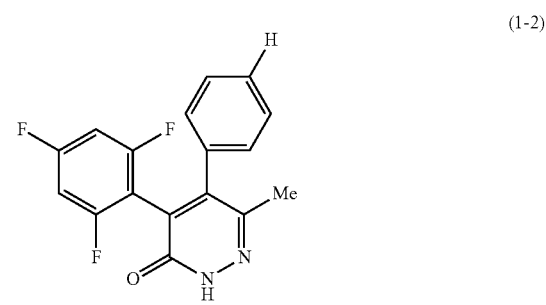

(1-2)

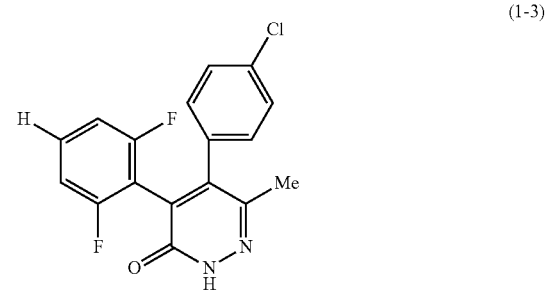

(1-3)

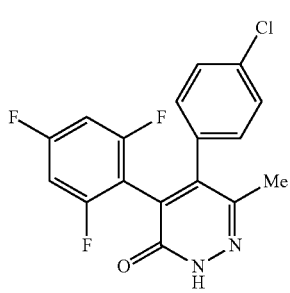

(1-4)

As mentioned in detail above, the compound (1) can be obtained by any one of the following steps.

A process comprising a step of reacting the compound (2) and the compound (3) in the presence of a Lewis acid to obtain an adduct, and a step of reacting the adduct obtained in the above-described step and hydrazine to obtain the compound (1), A process comprising reacting the compound (4) and hydrazine A process comprising reacting the compound (5) and hydrazine The compound (1) can be converted to a compound of the formula (6) (hereinafter, referred to as compound (6));

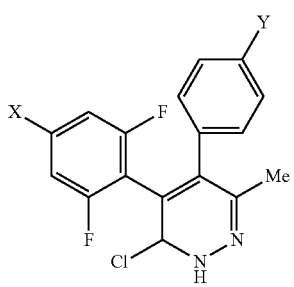

(6)

wherein X and Y have the same meanings as defined above, for example, by reacting the compound (1) and a chlorinating agent.

The reaction is publicly known, and the compound (6) can be produced by the method according to U.S. Pat. No. 7,569,518B2.

The reaction is carried out in the absence or presence of a solvent.

Examples of the solvent used in the reaction include hydrocarbon solvent such as toluene and xylene, halogenated hydrocarbon solvent such as chlorobenzene and 1,2-dichlorobenzene.

Examples of the chlorinating agent include phosphorus oxychloride and phosphorus pentachloride.

The amount of the chlorinating agent used in the reaction is usually a proportion of 1 to 20 moles per 1 mole of the compound (1).

The reaction temperature is usually in a range of from 20 to 120° C., and the reaction time is usually in a range of from 1 to 100 hours.

After completion of the reaction, for example, the reaction mixture is subjected to a post treatment operation such as the reaction mixture being concentrated, water being added to the residue and extracting with an organic solvent, and the resulting organic layer being dried, concentration and the like; thus, the compound (6) can be isolated. The compound (6) isolated can also be further purified by chromatography, re-crystallization and the like.

Next, specific examples of the compound (4) are shown.

Compounds represented by the formula (4-a)

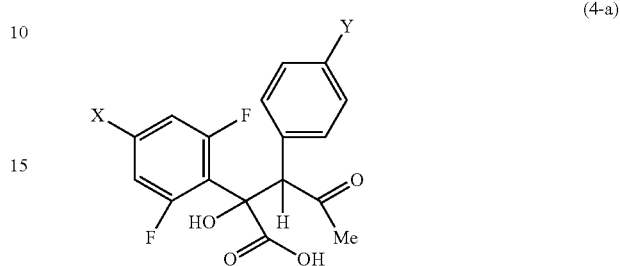

(4-a)

In the above formula, X and Y represent a combination of elements defined in Table 1.

TABLE 1

| X | Y |
|---|---|
| H | H |
| H | Cl |
| F | H |
| F | Cl |

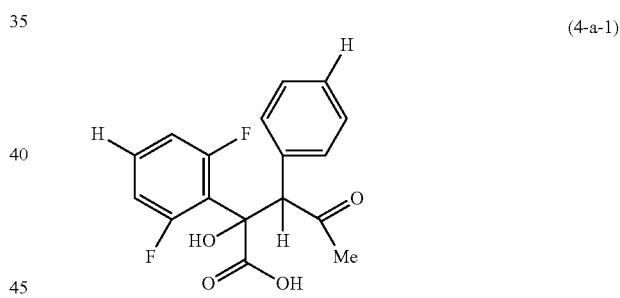

(4-a-1)

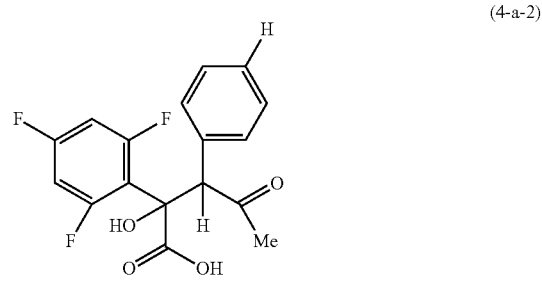

(4-a-2)

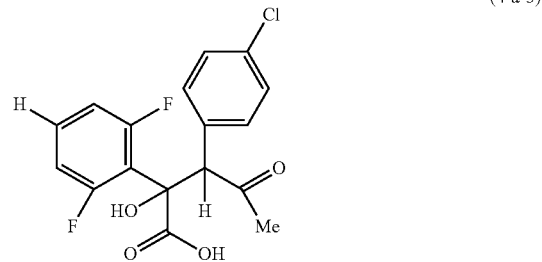

(4-a-3)

-continued
(4-a-4)
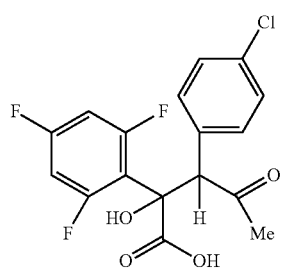
Compounds represented by the formula (4-b)
(4-b)
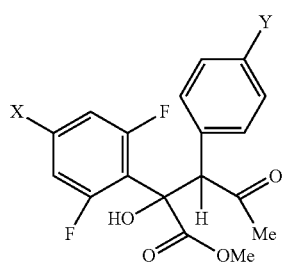
In the above formula, X and Y represent a combination of elements defined in Table 1.
(4-b-1)
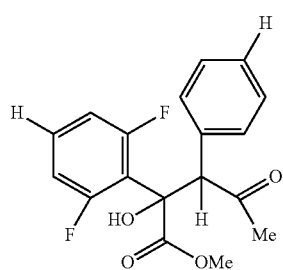
(4-b-2)
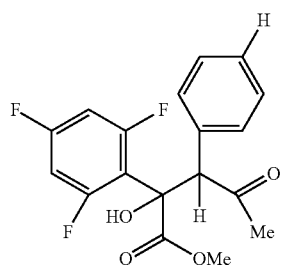
(4-b-3)
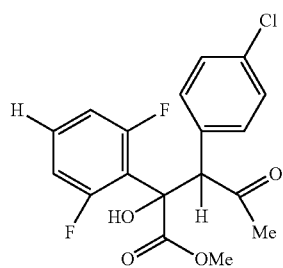
-continued
(4-b-4)
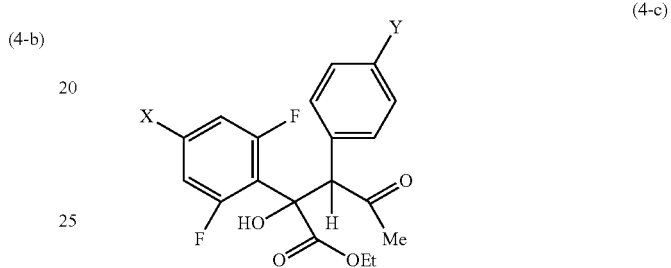
Compounds represented by the formula (4-c)
(4-c)
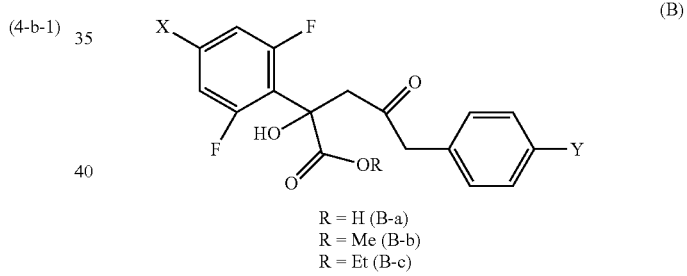
In the above formula, X and Y represent a combination of elements defined in Table 1. Examples of the compound (B) include the following compounds.
(B)
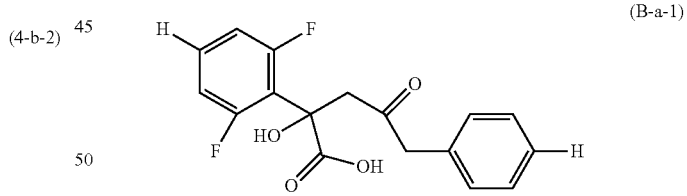
R = H (B-a)
R = Me (B-b)
R = Et (B-c)
(B-a-1)
(B-a-2)
(B-a-3)
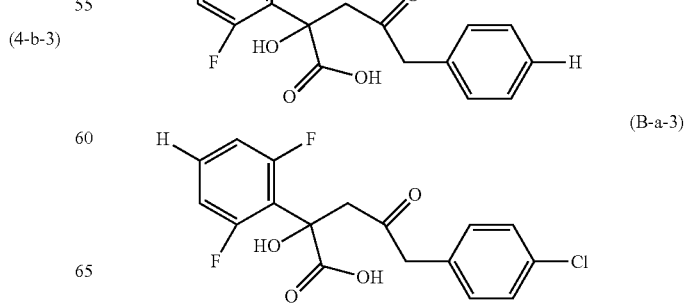

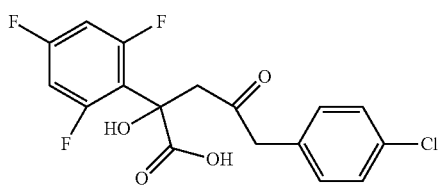

(B-a-4)

EXAMPLES

The present invention will be explained further in detail by examples below, but the present invention is not limited to these examples.

Example 1

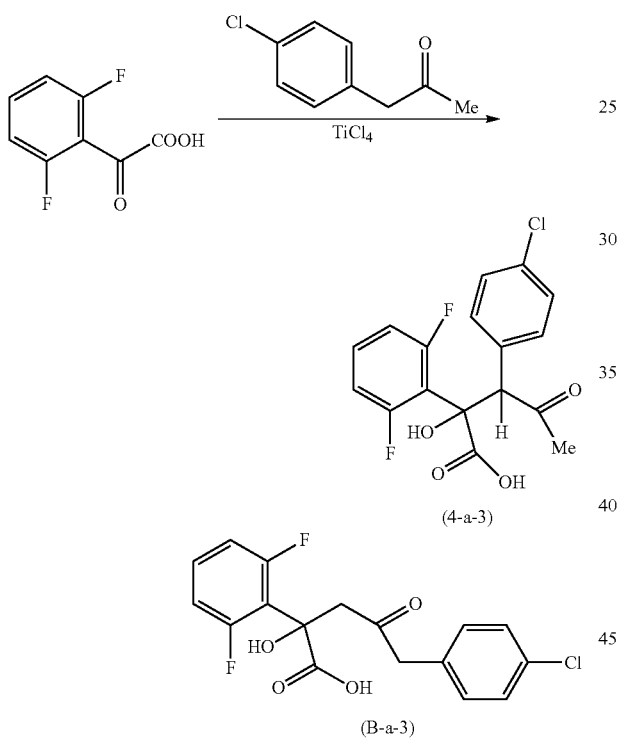

Two hundred and five (205) mg of 2,6-difluorobenzoyl-formic acid and 208 mg of 4-chlorophenylacetone were mixed with 0.5 ml of toluene, and 1.5 ml of 1 M toluene solution of titanium tetrachloride was added thereto at 50° C. under nitrogen atmosphere. The mixture was stirred at 50° C. for 4 hours. The stirred mixture was analyzed with high performance liquid chromatography to find out that area percentage of 3-(4-chlorophenyl)-2-(2,6-difluorophenyl)-2-hydroxy-4-oxopentanoic acid (hereinafter, referred to as compound (4-a-3)) is 76.1%, and area percentage of a compound of the formula (B-a-3) is 0.8%. The reaction mixture was left to cool, about 3 ml of ice water was added thereto, and then the liquid was subjected to liquid separation to obtain an organic layer and an aqueous layer. The organic layer was dried over anhydrous sodium sulfate, then, concentrated under reduced pressure. Four hundred and twenty (420) mg of the residue was subjected to silica gel column chromatography (elution solvent: hexane-methyl tert-butyl ether (hereinafter, methyl tert-butyl ether is referred to as MTBE)), to obtain 312 mg of the compound (4-a-3)) (yield: 80%).

Compound (4-a-3)

$^1$H-NMR (CDCl$_3$, TMS) δ (ppm): 2.22 (3H, br s), 4.80 (1H, br), 5.30 (1H, br), 6.82-6.87 (3H, m), 7.13-732 (5H, m).

LC-MS (ESI+APCI) MS-353 (M-1)

Example 2

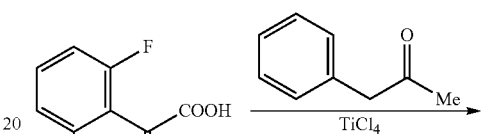

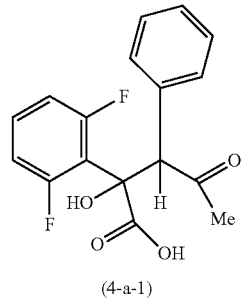

(4-a-1)

Two hundred and five (205) mg of 2,6-difluorobenzoyl-formic acid and 165 mg of phenylacetone are mixed with 0.5 ml of toluene, and 1.5 ml of a 1 M toluene solution of titanium tetrachloride is added thereto at 50° C. under nitrogen atmosphere. The mixture is stirred at 50° C. for 4 hours, then, left to cool, about 3 ml of ice water is added thereto, and the liquid is subjected to liquid separation to obtain an organic layer and an aqueous layer. The organic layer is dried over anhydrous sodium sulfate, then, concentrated under reduced pressure. The residue is subjected to silica gel column chromatography (elution solvent: hexane-MTBE), to obtain 2-(2,6-difluorophenyl)-2-hydroxy-4-oxo-3-phenylpentanoic acid (hereinafter, referred to as compound (4-a-1)).

Example 3

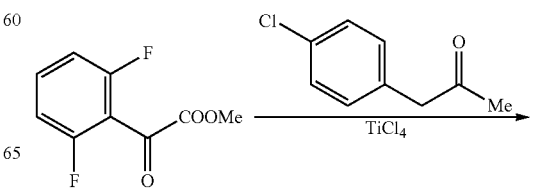

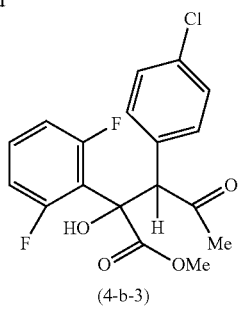

(4-b-3)

Two hundred twenty (220) mg of methyl 2,6-difluorobenzoylformate and 0.17 g of 4-chlorophenylacetone were mixed with 6 ml of toluene, and 1.73 g of titanium tetrachloride was added thereto at room temperature under nitrogen atmosphere. The mixture was stirred at room temperature for 1 day, then, 6 ml of toluene was additionally added thereto and the mixture was further stirred at room temperature for 3 days. Ice water was added thereto, and extraction with MTBE was performed. The organic layer obtained in the extraction was washed with water twice, dried over anhydrous magnesium sulfate, then, concentrated under reduced pressure. Zero point three seven (0.37) g of the residue obtained was subjected to silica gel column chromatography (elution solvent: hexane-ethyl acetate), to obtain 0.22 g of methyl 3-(4-chlorophenyl)-2-(2,6-difluorophenyl)-2-hydroxy-4-oxopentanoate (hereinafter, referred to as compound (4-b-3)) (yield: 60%).

Compound (4-b-3)

$^1$H-NMR (CDCl$_3$, TMS) δ (ppm): 2.30 (3H, s), 3.80 (3H, s), 4.46 (1H, s), 6.29 (1H, s), 6.67-6.73 (2H, m), 7.07 (2H, d), 7.07-7.16 (1H, m), 7.16 (2H, d).

Example 4

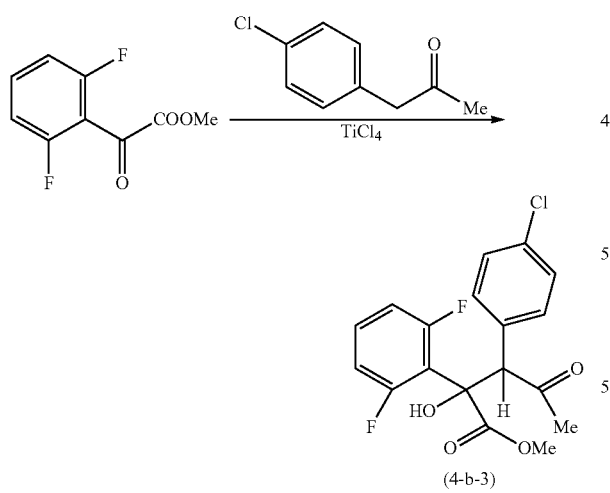

(4-b-3)

Two hundred and twenty three (223) mg of methyl 2,6-difluorobenzoylformate and 192 mg of 4-chlorophenylacetone were mixed with 1.0 mL of toluene, and 1.1 mL of a 1 M toluene solution of titanium tetrachloride was added thereto at 50° C. under nitrogen atmosphere. The mixture was stirred with heating at 50° C. for 3.5 hours, then, at 80° C. for 2 hours, then, left to cool, and about 1 mL of water and about 1 mL of ethyl acetate were added thereto, the mixture was allowed to stand still at room temperature overnight, then, the liquid was subjected to liquid separation to obtain an organic layer and an aqueous layer. The organic layer was dried over anhydrous sodium sulfate, then, concentrated under reduced pressure. Four hundred and thirty five (435) mg of the residue obtained was subjected to silica gel column chromatography (elution solvent: hexane-MTBE), to obtain 306.1 mg of a compound (4-b-3) (yield: 75.2%).

Example 5

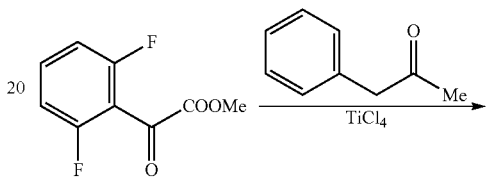

(4-b-1)

Two hundred and twenty three (223) mg of methyl 2,6-difluorobenzoylformate and 153 mg of phenylacetone are mixed with 1.0 mL of toluene, and 1.1 mL of a 1 M toluene solution of titanium tetrachloride is added thereto at 50° C. under nitrogen atmosphere. The mixture is stirred with heating at 50° C. for 3.5 hours, and at 80° C. for 2 hours, then, left to cool, and about 1 mL of water and about 1 mL of ethyl acetate are added thereto, the mixture is allowed to stand still at room temperature overnight, then, the liquid is subjected to liquid separation to obtain an organic layer and an aqueous layer. The organic layer is dried over anhydrous sodium sulfate, then, concentrated under reduced pressure. The residue obtained is subjected to silica gel column chromatography (elution solvent: hexane-MTBE), to obtain a compound of the formula (4-b-1) (hereinafter referred to as compound (4-b-1)).

Example 6

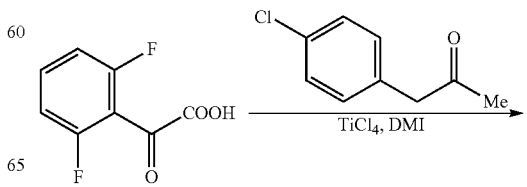

-continued

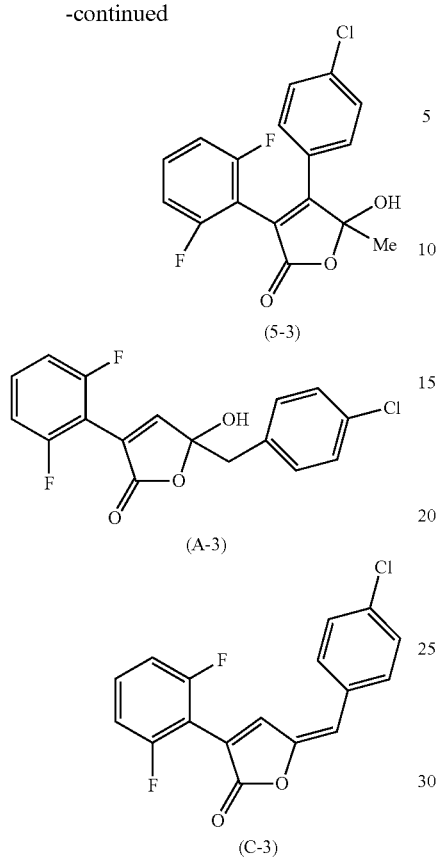

One hundred and eighty seven (187) mg of 2,6-difluorobenzoylformic acid and 180 mg of 4-chlorophenylacetone were mixed with 1.0 mL of DMI, and 0.2 mL of 1 M toluene solution of titanium tetrachloride was added thereto at 140° C. under nitrogen atmosphere. The mixture was stirred with heating at 140° C. for 2 hours, then, left to cool. Water and toluene were added thereto and the added mixture was stirred for a while, then, was allowed to stand still at room temperature overnight, and the liquid was subjected to liquid separation to obtain an organic layer and an aqueous layer. The organic layer was analyzed with high performance liquid chromatography to find out that area percentage of 4-(4-chlorophenyl)-3-(2,6-difluorophenyl)-5-hydroxy-5-methyl-2(5H)-furanone (hereinafter referred to as compound (5-3)) was 58.0%, area percentage of a compound of the formula (A-3) (hereinafter referred to as compound (A-3)) was 0.1%, and area percentage of a compound of the formula (C-3) (hereinafter referred to as compound (C-3)) was 6.8%. The organic layer was dried over anhydrous sodium sulfate, then, concentrated under reduced pressure. Five hundred and fifty three (553) mg of the residue obtained was subjected to silica gel column chromatography (elution solvent: hexane-MTBE), to obtain 229 mg of the compound (5-3) (yield: 67.5%).

Compound (5-3)

$^1$H-NMR (CDCl$_3$, TMS) δ (ppm): 1.77 (3H, s), 4.36 (1H, s), 6.84 (1H, t, J=8.6 Hz), 7.04 (1H, t, J=8.6 Hz), 7.28-7.32 (2H, m), 7.34-7.42 (1H, m), 7.47-7.51 (2H, m).

Compound (C-3)

1H-NMR (CDCl3, TMS) δ (ppm): 6.11 (1H, s), 7.01 (2H, t, J=8.1 Hz), 7.44-7.37 (3H, m), 7.62 (1H, s), 7.80-7.75 (2H, m).

Example 7

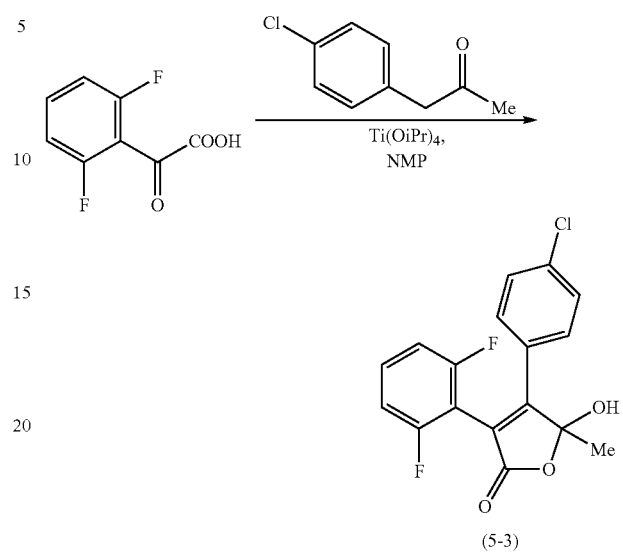

Nine hundred and eighty (980) mg of 2,6-difluorobenzoylformic acid, 4.0 g of toluene and 1.0 g of NMP were mixed, and 0.16 mL of titanium tetraisopropoxide was added thereto under nitrogen atmosphere. Nine hundred and eighty (980) mg of p-chlorophenylacetone was added dropwise thereto at 100° C. under reduced pressure with refluxing and dehydrating the mixture using Dean-Stark apparatus. The added mixture was stirred at 100° C. for 8 hours with reflux and dehydration. The resultant mixture was analyzed with high performance liquid chromatography to find out that area percentage of the compound (5-3) was 50.4%.

Example 8

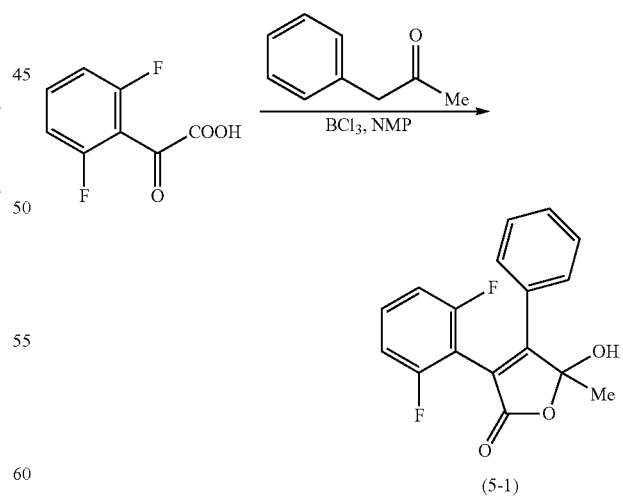

Nine hundred and eighty (980) mg of 2,6-difluorobenzoylformic acid, 4.0 g of toluene and 1.1 g of NMP were mixed, and 0.53 mL of 1.1 M toluene solution of boron trichloride was added thereto under nitrogen atmosphere. Seven hundred and eighty (780) mg of phenylacetone was added dropwise thereto at 100° C. under reduced pressure with refluxing and dehydrating the mixture using Dean-Stark apparatus. One point five nine (1.59) mL of 1.1 M toluene solution of boron trichloride was further added thereto at 100° C. for 39 hours with stir, reflux and dehydration. The added mixture was left to cool, 20% hydrochloric acid and toluene were added thereto, the resultant mixture was subjected to liquid separation to obtain an organic layer and an aqueous layer, and then the organic layer was concentrated to obtain 3-(2,6-difluorophenyl)-5-hydroxy-5-methyl-4-phenyl-2(5H)-furanone (hereinafter, referred to as compound (5-1)) (color and condition: brown liquid, yield: 63.8%).

Example 9

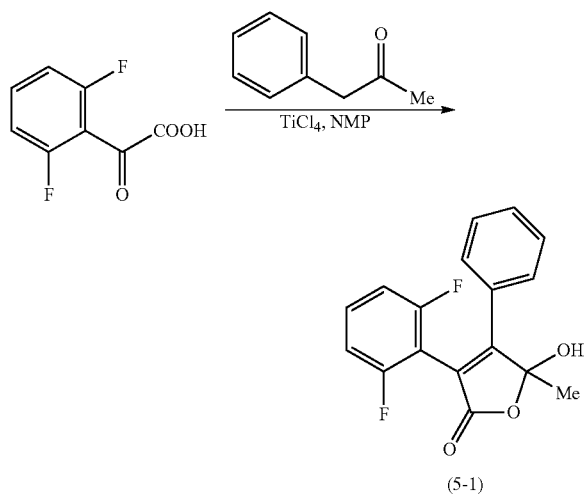

(5-1)

Nine hundred and seventy (970) mg of 2,6-difluorobenzoylformic acid, 4.0 g of toluene and 1.0 g of NMP were mixed, and 0.52 mL of 1.1 M toluene solution of titanium tetrachloride was added thereto under nitrogen atmosphere. Seven hundred and sixty (760) mg of phenylacetone was added thereto at 100° C. under reduced pressure with refluxing and dehydrating the mixture using Dean-Stark apparatus. The added mixture was left to cool, 20% hydrochloric acid and toluene were added thereto, the resultant mixture was subjected to liquid separation to obtain an organic layer and an aqueous layer, and then the organic layer was concentrated to obtain the compound (5-1) (yield: 77.4%) as brown liquid.

Example 10

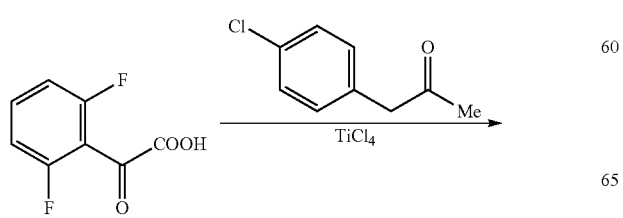

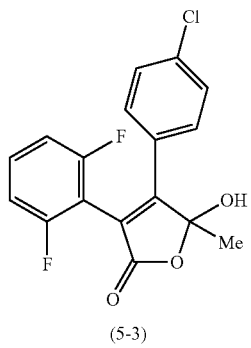

(5-3)

Nine hundred and seventy (970) mg of 2,6-difluorobenzoylformic acid and 4.0 g of toluene were mixed, and 0.53 mL of 1 M toluene solution of titanium tetrachloride was added thereto under nitrogen atmosphere. Nine hundred and eighty (980) mg of p-chlorophenylacetone was added thereto at 100° C. under reduced pressure with refluxing and dehydrating the mixture using Dean-Stark apparatus, and then, the added mixture was stirred at 100° C. for 7 hours with reflux and dehydration under reduced pressure. The stirred mixture was left to cool, 20% hydrochloric acid and toluene were added thereto, the resultant mixture was subjected to liquid separation, and then the organic layer was concentrated to obtain brown solid containing the compound (5-3) (yield: 27.6%). Recovery of 2,6-difluorobenzoylformic acid was 39.9%.

Example 11

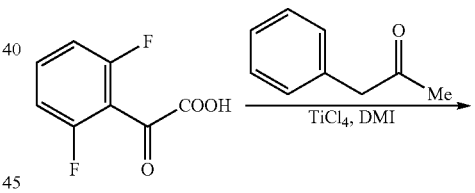

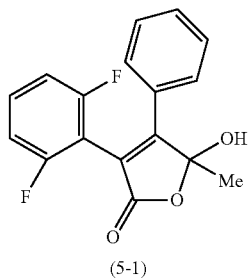

(5-1)

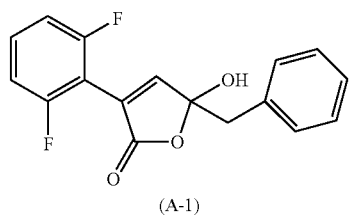

(A-1)

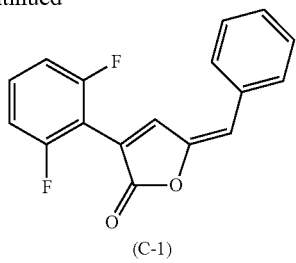

(C-1)

One hundred and eighty seven (187) mg of 2,6-difluorobenzoylformic acid and 143 mg of phenylacetone are mixed with 1.0 mL of DMI, and 0.2 mL of 1 M toluene solution of titanium tetrachloride is added thereto at 140° C. under nitrogen atmosphere. The mixture is stirred with heating at 140° C. for 2 hours, then, left to cool. Water and toluene are added thereto and the added mixture is stirred for a while, then, the stirred mixture is allowed to stand still at room temperature overnight, then, the liquid is subjected to liquid separation to obtain an organic layer and an aqueous layer. The organic layer is analyzed with high performance liquid chromatography to find out the compound (5-1), a compound of the formula (A-1) and a compound of the formula (C-1). The organic layer is dried over anhydrous sodium sulfate, then, concentrated under reduced pressure. The residue obtained is subjected to silica gel column chromatography (elution solvent: hexane-MTBE), to obtain the compound (5-1).

Example 12

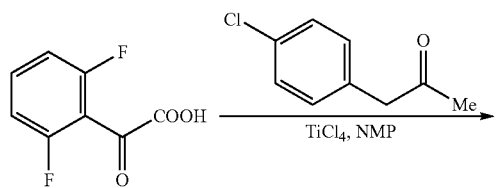

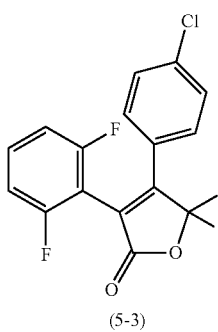

(5-3)

One hundred and ninety four (194) mg of 2,6-difluorobenzoylformic acid and 178 mg of 4-chlorophenylacetone were mixed with 1.0 mL of xylene, and 0.1 mL of a 1 M toluene solution of titanium tetrachloride, then, 0.3 ml of NMP were added thereto at room temperature under a nitrogen atmosphere. The mixture was stirred with heating at 120° C. for 4 hours, then, left to cool. Diluted hydrochloric acid and toluene were added thereto and the added mixture was subjected to liquid separation to obtain the first organic layer and an aqueous layer. The aqueous layer was extracted once more to obtain the second organic layer, and the first and second organic layers were combined, and dried over anhydrous sodium sulfate, then, concentrated under reduced pressure. The resultant residue was subjected to silica gel column chromatography (elution solvent: hexane-MTBE), to obtain 253 mg of the compound (5-3) (yield: 72.0%).

Example 13

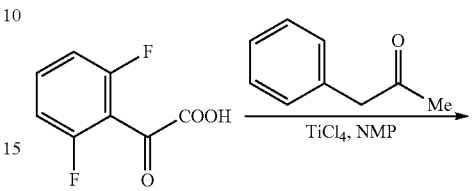

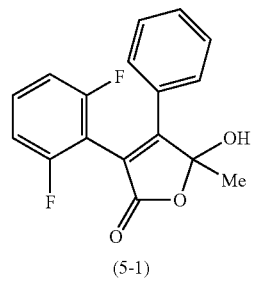

(5-1)

One hundred and ninety four (194) mg of 2,6-difluorobenzoylformic acid and 142 mg of phenylacetone are mixed with 1.0 mL of xylene, and 0.1 mL of a 1 M toluene solution of titanium tetrachloride, then, 0.3 mL of NMP are added thereto at room temperature under nitrogen atmosphere. The mixture is stirred with heating at 120° C. for 4 hours, then, left to cool, dilute hydrochloric acid and toluene are added thereto, and the liquid is subjected to liquid separation to obtain the first organic layer and an aqueous layer. The aqueous layer is extracted with toluene once more to obtain the second organic layer. The first and second organic layers are mixed, dried over anhydrous sodium sulfate, then, concentrated under reduced pressure. The resultant residue is subjected to silica gel column chromatography (elution solvent: hexane-MTBE), to obtain the compound (5-1).

Example 14

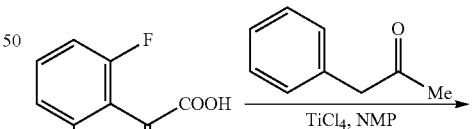

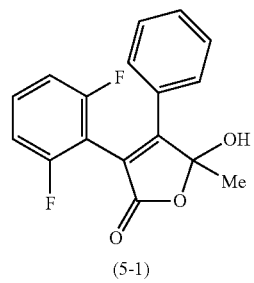

(5-1)

Six point eight eight (6.88) g of 2,6-difluorobenzoylformic acid, 8.1 mL of toluene and 7.2 mL of NMP were mixed, and 3.69 mL of 1 M toluene solution of titanium tetrachloride was added thereto under nitrogen atmosphere. Five point five two (5.52) g of phenylacetone was added thereto at 75° C. under reduced pressure with refluxing and dehydrating the mixture using Dean-Stark apparatus. The added mixture was stirred at 75° C. for 22 hours under reduced pressure with reflux and dehydration. The stirred mixture was left to cool, 7.0 g of 20% hydrochloric acid and 6.9 g of toluene were added thereto, and the resultant mixture was stirred, and then, subjected to liquid separation to obtain an organic layer and an aqueous layer. The organic layer was concentrated to obtain the compound (5-1) (yield: 91.4%) brown liquid.

Example 15

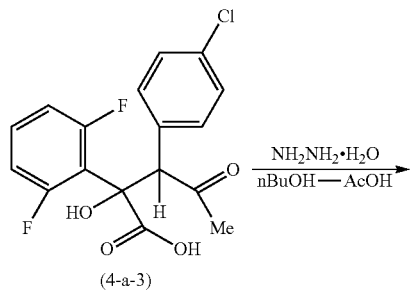
(4-a-3)

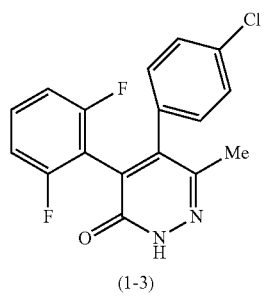
(1-3)

Zero point two zero (0.20) g of the compound (4-a-3) was added to 4 ml of n-butanol and 0.4 ml of acetic acid, and 35 mg of hydrazine mono-hydrate was added thereto, and the mixture was stirred at room temperature for 1 hour. Thereafter, the stirred mixture was heated at 100° C. for 6 hours, further, heated under reflux for 6 hours. After the resultant mixture was left to cool, the precipitated solid was collected by filtration, and washed with mixed liquid (1:1) of MTBE-hexane, to obtain 0.13 g of 5-(4-chlorophenyl)-4-(2,6-difluorophenyl)-6-methyl-2H-pyridazin-3-one (hereinafter, referred to as compound (1-3)) (yield: 69%).

Compound (1-3)

$^1$H-NMR (CDCl$_3$, TMS) δ (ppm): 2.12 (3H, s), 6.77-6.81 (2H, m), 7.01-7.04 (2H, m), 7.19-7.28 (3H, m), 11.61 (1H, br s)

The compound of the formula (1) was isolated as by product.

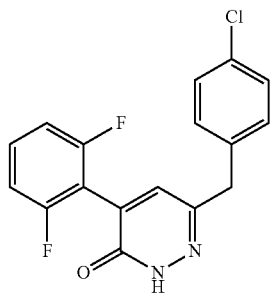
(I)

Compound (1)

$^1$H-NMR (CDCl3, TMS) δ (ppm): 3.94 (2H, s), 6.94-7.00 (2H, m), 7.14-7.18 (3H, m), 7.26-7.40 (3H, m), 11.12 (1H, br s)

Example 16

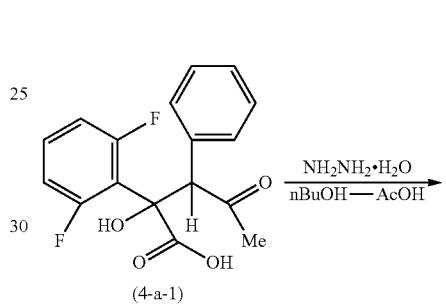
(4-a-1)

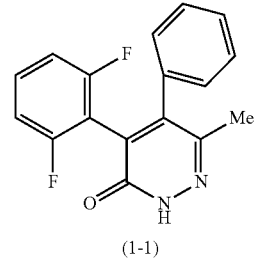
(1-1)

Zero point one eight (0.18) g of the compound (4-a-1) is added to 4 ml of n-butanol and 0.4 ml of acetic acid, and 35 mg of hydrazine mono-hydrate is added thereto, and the mixture is stirred at room temperature for 1 hour. Thereafter, the reaction mixture is heated at 100° C. for 6 hours, further, heated under reflux for 6 hours. After the resultant mixture was left to cool, the precipitated solid is collected by filtration, and washed with mixed liquid (1:1) of MTBE-hexane, to obtain 4-(2,6-difluorophenyl)-5-methyl-6-phenyl-2H-pyridazin-3-one (hereinafter, referred to as compound (1-1)).

Example 17

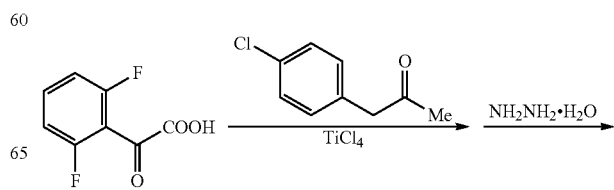

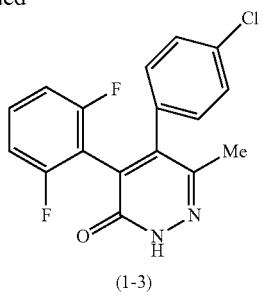

(1-3)

A mixture of 400 mg of 2,6-difluorobenzoylformic acid and 388 mg of 4-chlorophenylacetone was stirred under nitrogen atmosphere, and 2.2 mL of 1 M toluene solution of titanium tetrachloride was added thereto at room temperature. The mixture was stirred with heating at 50° C. for 2.5 hours, then, 1.0 mL of water was added, and the mixture was further stirred for 0.5 hours, then, left to cool to room temperature, and the liquid was subjected to liquid separation to obtain an organic layer and an aqueous layer. One hundred and forty five (145) mg of hydrazine monohydrate was added to the organic layer while stirred, and the mixture was stirred with heating at 100° C. for 5.5 hours, then, 0.2 mL of acetic acid was added, and the added mixture was further stirred with heating for 5.5 hours. After the resultant mixture was left to cool to room temperature, ethyl acetate and dilute hydrochloric acid were added thereto, and the liquid was subjected to liquid separation to obtain an organic layer and an aqueous layer. The organic layer was dried over anhydrous sodium sulfate, then, concentrated under reduced pressure. The resultant residue was dispersed in about 5 mL of methanol, and filtration thereof was performed. The residue on the filter was dried under reduced pressure, to obtain 281 mg of the compound (1-3). The filtrate was concentrated under reduced pressure, and the residue was subjected to silica gel column chromatography (elution solvent: hexane-MTBE), to obtain 281 mg of the compound (1-3). Total amount of the compound (1-3): 562 mg. Yield: 78%.

Example 18

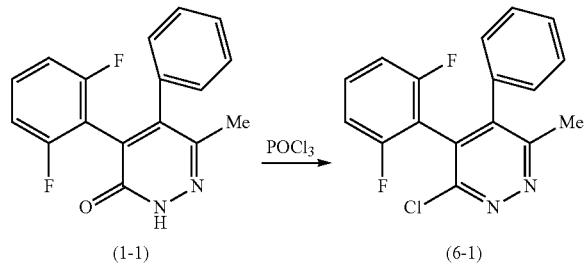

Fifty point zero zero (50.00) g of the compound (1-1) and 100.0 g of toluene were mixed, and 30.5 g of phosphorus oxychloride was added dropwise at 100° C. under nitrogen atmosphere. The added mixture was stirred at 100° C. for 8 hours. After being left to cool, the reaction mixture was added dropwise in 100.1 g of water. Forty nine point nine (49.9) g of toluene was added thereto, and 65.8 g of 48% aqueous sodium hydroxide solution was added dropwise thereto. The resultant mixture was subjected to liquid separation to obtain an organic layer and an aqueous layer. The organic layer was washed with 71.6 g of water and concentrated to obtain 2-chloro-4-phenyl-3-(2,6-difluorophenyl)-5-methyl-pyridazine (hereinafter, referred to as compound (6-1)) (yield: 100%).

Reference Production Example 1

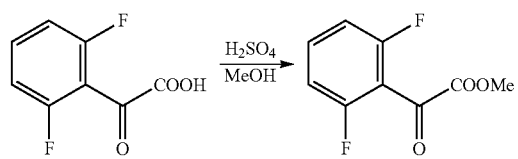 [SMILES: "MeOH" ; O=C(O)C(=O)c1c(F)cccc1F ; "H2SO4" ; COC(=O)C(=O)c1c(F)cccc1F]

One point eight six (1.86) g of 2,6-difluorobenzoylformic acid [$^1$H-NMR (CDCl$_3$, TMS) 6.56 (1H, br s), 6.98-7.09 (2H, m), 7.53-7.63 (1H, m)] was mixed with 21 mL of methanol, and 0.1 mL (0.184 g) of concentrated sulfuric acid was added thereto at room temperature under nitrogen atmosphere. The mixture was stirred at room temperature for 2 days, then, concentrated. Ice water was added thereto, and extraction with MTBE was performed. The organic layer obtained in the extraction was washed with water twice, dried over anhydrous magnesium sulfate, then, concentrated under reduced pressure. The resultant residue (1.78 g) was subjected to silica gel column chromatography (elution solvent: hexane-ethyl acetate), to obtain 1.64 g of methyl 2,6-difluorobenzoylformate (yield: 82%) as colorless liquid.

$^1$H-NMR (CDCl$_3$, TMS) δ (ppm): 3.96 (3H, s), 6.99-7.04 (2H, m), 7.52-7.60 (1H, m).

Reference Production Example 2

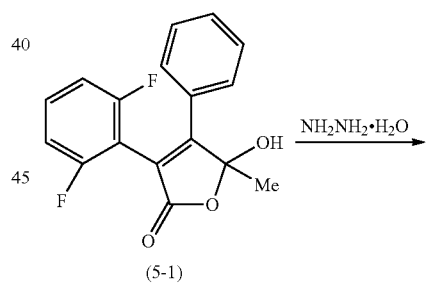

(5-1)

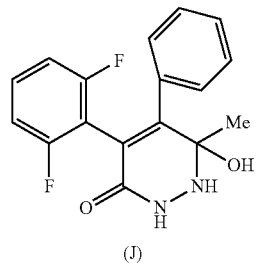

(J)

One point zero zero (1.00) g of the compound (5-1) was mixed with 5.1 g of toluene, and 0.2 g of hydrazine monohydrate was added thereto at room temperature under nitrogen atmosphere. The mixture was stirred at room temperature for 10 hours. The resultant mixture was cooled by soaking the vessel containing the mixture in an ice bath to precipitate crystals, and the crystals were collected by filtration, washed with toluene, and dried to obtain a compound of the formula (J) (hereinafter referred to as compound (J)) (yield: 87.3%).

Compound (J)

1H-NMR (CDCl3, TMS) δ (ppm): 3.18 (3H, s), 3.76 (1H, br), 4.02 (2H, br), 6.80 (1H, t), 6.99 (1H, t), 7.25-7.36 (4H, m), 7.48-7.54 (2H, m)

Reference Production Example 3

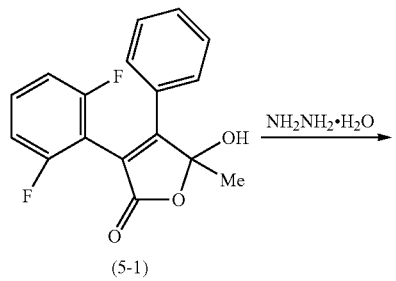

(5-1)

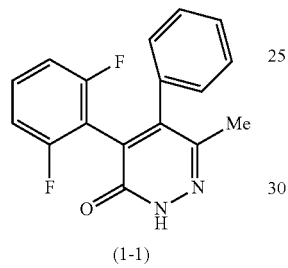

(1-1)

Seven point eight four (7.84) g of the compound (5-1) was mixed with 12.2 g of toluene, and 2.14 g of hydrazine monohydrate was added thereto at room temperature under nitrogen atmosphere, and the mixture was heated and refluxed at 100° C. for 29 hours. The compound of the formula (J) was found out in the course of the reaction with high performance liquid chromatography. After the reaction mixture was left to cool, 6.06 g of 10% hydrochloric acid was added thereto, precipitated solid was collected by filtration. After washing with toluene and water, the solid was dried to obtain the compound (1-1) (yield: 94.5%).

The invention claimed is:

1. A compound of the formula (4);

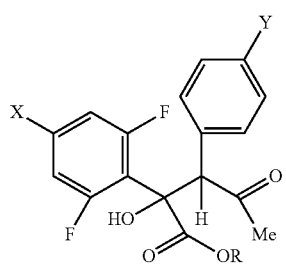

(4)

wherein X represents a hydrogen atom, a fluorine atom, a chlorine atom or a bromine atom, Y represents a hydrogen atom, a fluorine atom, a chlorine atom or a bromine atom, and R represents a hydrogen atom or a C1-C4 alkyl group.

2. A process for producing a compound of the formula (1);

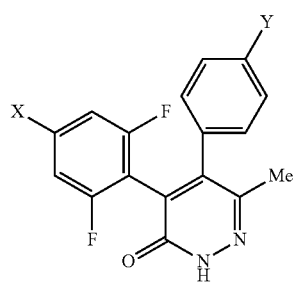

(1)

wherein X represents a hydrogen atom, a fluorine atom, a chlorine atom or a bromine atom, and Y represents a hydrogen atom, a fluorine atom, a chlorine atom or a bromine atom;

which comprises step 1 of reacting a compound of the formula (2) and a compound of the formula (3) in the presence of a Lewis acid to obtain an adduct;

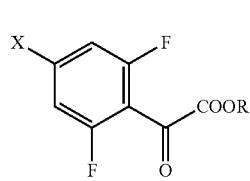

(2)

wherein R represents a hydrogen atom or a C1-C4 alkyl group and X has the same meaning as defined above,

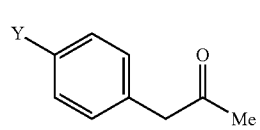

(3)

wherein Y has the same meaning as defined above;

and step 2 of reacting the adduct obtained in the step 1 and hydrazine.

3. The process according to claim 2, wherein the adduct is a compound of the formula (5);

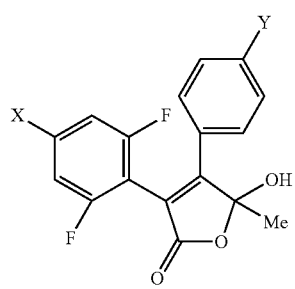

(5)

wherein X and Y have the same meanings as defined above.

4. The process according to claim 2, wherein the reaction of the compound of the formula (2) and the compound of the formula (3) is conducted in the presence of a polar aprotic solvent.

5. The process according to any one of claims 2 to 4, wherein the Lewis acid is a titanium compound or a boron compound.

6. The process according to claim 2, 3 or 4, wherein the reactions both in step 1 and step 2 are carried out in the presence of an aromatic hydrocarbon solvent.

7. A process for producing a compound represented by the formula (1);

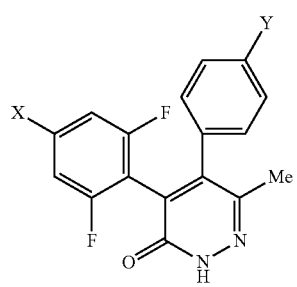
(1)

wherein X represents a hydrogen atom, a fluorine atom, a chlorine atom or a bromine atom, and Y represents a hydrogen atom, a fluorine atom, a chlorine atom or a bromine atom;

which comprises reacting a compound of the formula (4) and hydrazine;

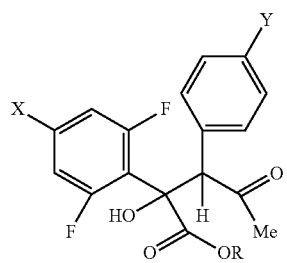
(4)

wherein R represents a hydrogen atom or a C1-C4 alkyl group and X and Y have the same meanings as defined above.

8. The process according to claim 7, wherein the reaction is carried out in the presence of an aromatic hydrocarbon solvent.

9. A process according to claim 7, which further comprises reacting the compound of formula (1) and a chlorinating agent to produce a compound of the formula (6);

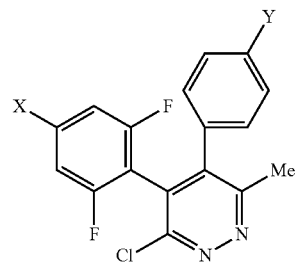
(6)

wherein X and Y are the same as defined for formula (1).

10. A process for producing a compound of the formula (4);

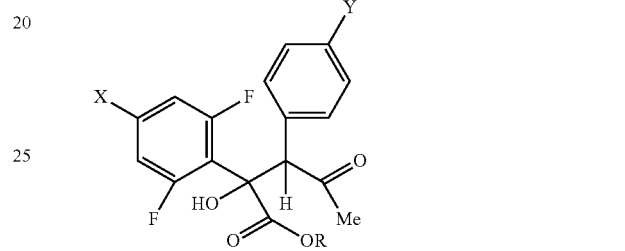
(4)

wherein X represents a hydrogen atom, a fluorine atom, a chlorine atom or a bromine atom, Y represents a hydrogen atom, a fluorine atom, a chlorine atom or a bromine atom, and R represents a hydrogen atom or a C1-C4 alkyl group;

which comprises reacting a compound of the formula (2) and a compound of the formula (3) in the presence of a Lewis acid in range of from 20 to 80° C.;

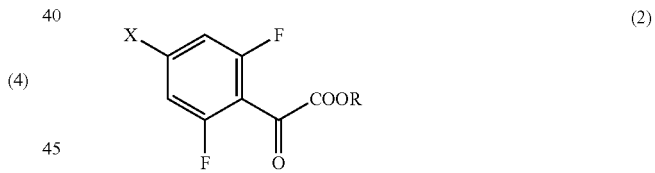
(2)

wherein X and R have the same meanings as defined above,

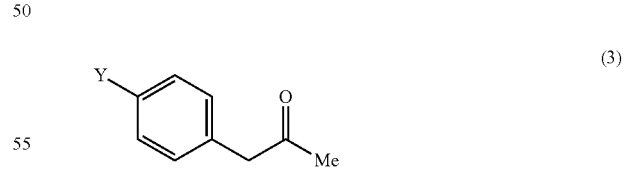
(3)

wherein Y has the same meaning as defined above.

11. The process according to claim 10, wherein the Lewis acid is a titanium compound or a boron compound.

12. The process according to claim 10 or 11, wherein the reaction is carried out in the presence of an aromatic hydrocarbon solvent.

13. The process according to claim 3, wherein the reaction of the compound of the formula (2) and the compound of the formula (3) is conducted in the presence of a polar aprotic solvent.

14. The process according to claim 5, wherein the reactions both in step 1 and step 2 are carried out in the presence of an aromatic hydrocarbon solvent.

\* \* \* \* \*